United States Patent
Klempau

(10) Patent No.: US 6,745,769 B2
(45) Date of Patent: Jun. 8, 2004

(54) RESPIRATION BAG

(75) Inventor: Hans-Jürgen Klempau, Bad Schwartau (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 18 days.

(21) Appl. No.: 10/066,743

(22) Filed: Feb. 6, 2002

(65) Prior Publication Data
US 2002/0108612 A1 Aug. 15, 2002

(30) Foreign Application Priority Data
Feb. 10, 2001 (DE) .................................. 101 06 009

(51) Int. Cl.$^7$ ................................................ A62B 9/00
(52) U.S. Cl. ............................ 128/205.13; 128/205.14
(58) Field of Search ....................... 128/202.28, 202.29, 128/203.11, 204.18, 203.28, 205.13, 204.28, 205.14

(56) References Cited

U.S. PATENT DOCUMENTS

| | | | | |
|---|---|---|---|---|
| 3,046,978 A | * | 7/1962 | Lea | 128/205.13 |
| 3,356,100 A | * | 12/1967 | Seeler | 137/102 |
| 4,498,472 A | * | 2/1985 | Tanaka | 128/205.17 |
| 4,628,926 A | * | 12/1986 | Duncan et al. | 128/203.28 |
| 4,790,305 A | * | 12/1988 | Zoltan et al. | 128/200.23 |
| 4,898,166 A | * | 2/1990 | Rose et al. | 128/205.13 |
| 5,140,982 A | * | 8/1992 | Bauman | 128/205.13 |
| 5,163,424 A | * | 11/1992 | Kohnke | 128/205.13 |
| 5,318,016 A | * | 6/1994 | Mecikalski | 128/200.23 |
| 5,617,616 A | * | 4/1997 | Cutts, Sr. | 24/30.5 R |
| 5,645,056 A | * | 7/1997 | Pomeroy | 128/205.13 |
| 5,787,880 A | * | 8/1998 | Swanson et al. | 128/202.28 |

FOREIGN PATENT DOCUMENTS

DE  195 17 857  5/1996

\* cited by examiner

Primary Examiner—Aaron J. Lewis
Assistant Examiner—Mital Patel
(74) Attorney, Agent, or Firm—Walter Ottesen

(57) ABSTRACT

The invention relates to a respiration bag (1) which has at least one fold (2, 11) extending annularly over the bag (1). The respiration bag (1) can be bent in along this fold (2, 11). In this way, at least one depression results which leads to a reduced volume of the respiration bag (1). A flip over of the respiration bag from the bent-in position is prevented by sealing lips (10, 12) or additional mechanical holders which are applied from the outside to the at least one fold (2, 11). The respiration bag (1) remains stable in the bent-in position with reduced volume up to an inner pressure of 45 to 50 millibar. In this way, a respiration bag (1) for respiration volumes of different sizes is available in dependence upon, for example, whether respiration is to take place with ambient air or oxygen-enriched air or is dependent upon whether an adult or a child is to be respirated.

8 Claims, 1 Drawing Sheet

RESPIRATION BAG

Field of the Invention

The invention relates to a respiration bag having at least one connection stub.

BACKGROUND OF THE INVENTION

The artificial respiration of a patient ensures the adequate supply of oxygen and carbon dioxide discharge, for example, in connection with measures for resuscitation or for administering an anesthesia. One possibility of the artificial respiration is the use of a respiration bag. A respiration bag is disclosed in U.S. Patent 5,647,354. The respiration bag can be inflated or can fill because of its own reset forces and be pressed together in order to carry out the artificial respiration. The air reaches the patient via pressure applied with the hand on the resuscitation bag and via a respiration valve. Either a mask or a tube is selectively connected downstream of the respiration valve.

The known respiration bag includes a stub with which the respiration bag can be connected to an oxygen feed line. The respiration bag can be manually operated and belongs, for example, to the equipment of ambulances and operating rooms.

A varying volume is required in dependence upon whether the respiration bag functions for respiration with ambient air or with oxygen. For adults, the application of a smaller volume is required with the simultaneous supply of oxygen than is used for the respiration with ambient air. This requirement is based on recent investigations which were carried out by the AHA (American Heart Association) and the ERC (European Resuscitation Council).

The requirement for two different volumes, which are to be applied, is satisfied with the known respiration bags in that two types of respiration bags of different sizes are used. If there is a transfer from a respiration with ambient air to a respiration with ambient air supplemented with oxygen or, vice versa, then the procedure is made difficult in that the respiration bag must be exchanged for a respiration bag of a different size. For this reason, two types of respiration bags of different sizes must always be available for use.

SUMMARY OF THE INVENTION

It is an object of the invention to provide a respiration bag which is so improved that the application of different volumes for the respiration of a patient is possible with this bag.

The respiration bag of the invention has at least one connecting stub and includes: a bag-shaped hollow body defining an axis; at least one fold region extending annularly over the body; the bag-shaped body being foldable in the direction of the axis from a first stable position wherein the hollow body extends smoothly over the fold region to a second stable position wherein the bag-shaped body is bent inwardly in the direction of the axis at the fold region to define an annular fold in the fold region.

The respiration bag according to the invention includes at least one fold which extends annularly over the bag. The respiration bag including the at least one fold is, for example, made of elastomer, silicon or Neoprene and is stable as to form. The at least one fold can be set off from the remainder of the bag utilizing color or also a different texture of the material surface. With respect to the surface of the material of the bag, this can be, for example, smooth at the fold and be roughened over the remainder of the bag or be roughened at the fold and otherwise smooth. The material of the respiration bag in the region of the at least one fold can be exactly as thick as at remaining locations thereof or can also be thinner than the material outside the fold region. The respiration bag can be a disposable item or can be reusable. With the one fold or with each fold it is possible that the respiration bag assumes two different positions I and II with respect to this fold. In position I, the respiration bag extends smoothly over the particular fold and assumes its maximum volume, preferably in a size of between 1600 and 1800 milliliters. Such a volume is usual for the respiration of an adult with ambient air. In the position II, the respiration bag is bent in along the particular fold. A depression arises in the form of trough or basin which is annularly delimited by the bent-over fold. With this depression, the volume of the respiration bag is reduced, for example, to 1400 milliliters. This is the usual volume for the respiration of an adult with oxygen-enriched air.

A respiration bag, which can assume at least two different volumes, has the advantage that one can rapidly and simply provide the appropriate volume depending upon whether respiration is with ambient air or oxygen-enriched air. Compared to adults, a lesser volume for the respiration for ambient air as well as with oxygen-enriched air must be made available for children. The respiration of children can take place in this way with the same respiration bag which is also used for adults. As described above, the at least one fold on the respiration bag makes possible a position I with a maximum volume and a position II with a reduced volume. Especially the position II can be fixed with an advantageous configuration of the respiration bag of the invention.

In an advantageous embodiment, a sealing lip is provided along the fold on the inner wall surface of the respiration bag. This sealing lip runs essentially parallel to the inner wall of the respiration bag and has a free end which projects in the direction of that section of the respiration bag viewed from the fold which remains unchanged in positions I and II and is not bent in the form of a depression. When the respiration bag goes from position I with maximum volume to the volume-reduced position II, then the sealing lip at the affected fold, which is being bent over, moves toward and against the inner wall surface of the respiration bag. An unintended flip over of the respiration bag from position II into position I is thereby countered so that the inner pressure, which is present in the respiration bag and which can amount to up to 45 millibar, acts on the sealing lip positioned forward of the bent-over fold in lieu of against the bent-over fold itself. The stability of the respiration bag in the volume-reduced position II is ensured up to an inner pressure of 45 to 50 millibar. Only a powerful pull of the hand can bring the respiration bag from position II into position I.

In the second advantageous embodiment of the invention, the respiration bag can be fixed in the volume-reduced position II additionally by mechanical holders, for example, clamps which are distributed uniformly over the annularly-shaped bent-over fold. The clamps can be made of plastic or metal.

Two folds of the kind described above are provided in an additional embodiment of the respiration bag according to the invention which can have the shape of an ellipsoid. The two folds can, for example, extend parallelly to each other and lie on the axis of the largest longitudinal extension of the ellipsoid at different spacings from the two end points of the ellipsoid. Accordingly, there are four positions with four different volumes of the respiration bag which can be realized depending upon whether the bag is bent over at both folds, on a first one of the two folds, a second one of the two folds or at none of the folds.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
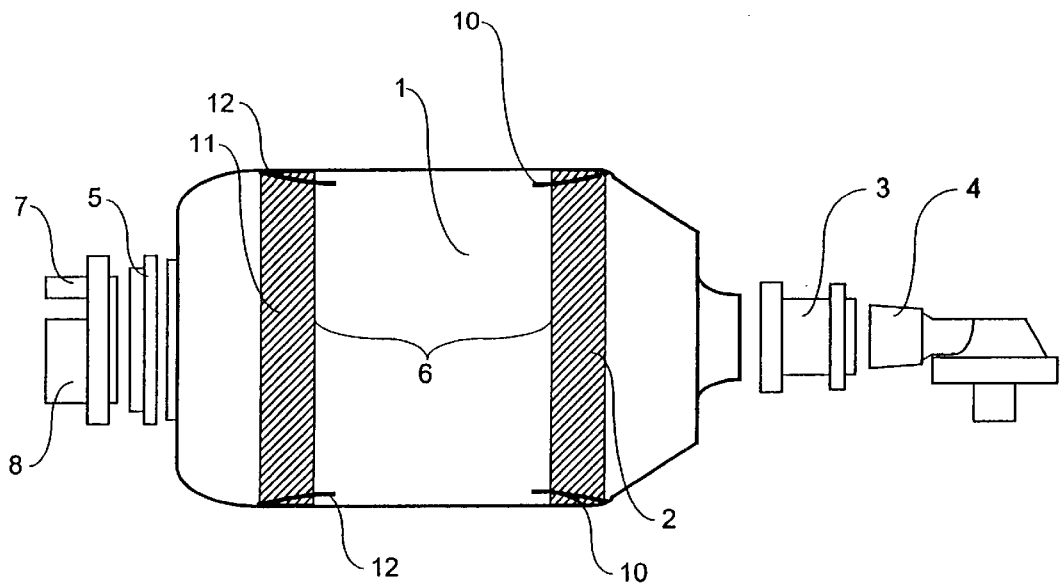
FIG. 1 is a side elevation view of a respiration bag in accordance with the invention in position I having maximum bag volume; and, FIG. 2 is a side elevation view of the respiration bag of FIG. 1 shown in position II with reduced bag volume.

In FIG. 1, a side elevation view of a respiration bag 1 is shown in position I having maximum bag volume. A first fold 2 and a second fold 11 extend annularly over the respiration bag 1. A first sealing lip 10 extends along the first fold 2 and a second sealing lip 12 extends along the second fold 11 on the inner wall surface of the respiration bag 1. The first sealing lip 10 and the second sealing lip 12 extend essentially parallel to the inner wall surface of the respiration bag 1. The free edge of the first sealing lip 10 and the free edge of the second sealing lip 12 project in the direction of that section 6 of the respiration bag 1 which remains unchanged for a form of the respiration bag of FIG. 1 in the position I with maximum bag volume as well as for a shape of the respiration bag 1 of FIG. 2 in position II with reduced bag volume. An intake valve 5 is disposed at a first connecting stub and a respiration valve 3 is disposed at a second connecting stub. A first connection 7 and a second connection 8 lead to the intake valve 5. Oxygen can be supplied via connection 7 and ambient air via connection 8. This ambient air can be enriched with oxygen as may be required. A connection 4 leads from the respiration valve 3 to a patient not shown in FIG. 1. The inhalation as well as the exhalation of the patient can take place via the respiration valve 3.

Figure 2:
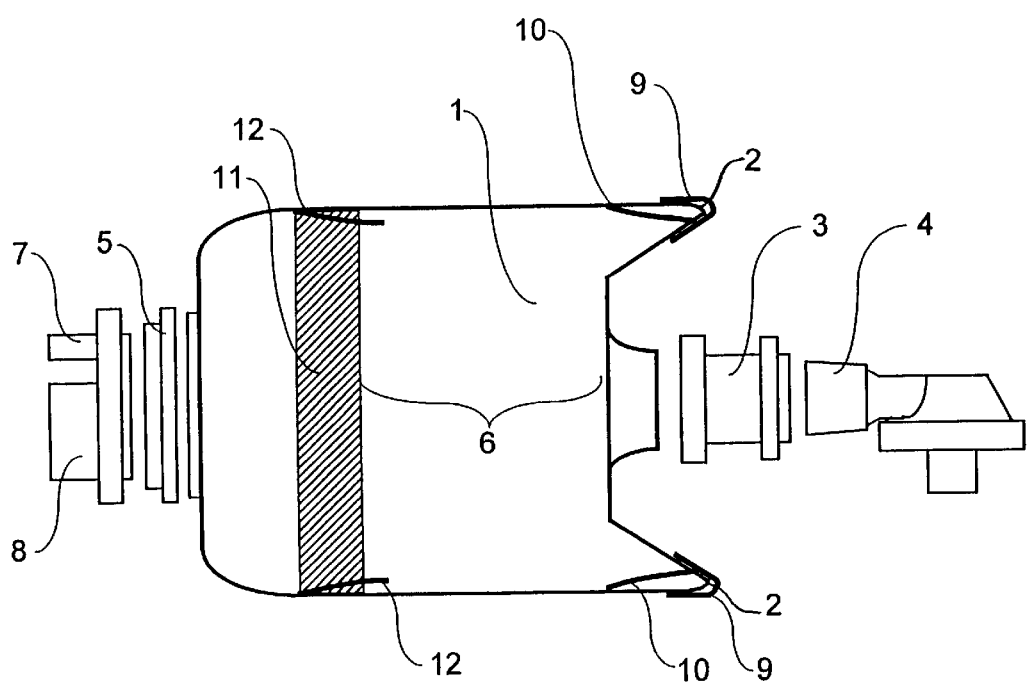

A side elevation section view of the respiration bag of FIG. 1 is shown in FIG. 2 in position II having a reduced bag volume. The surface of the respiration bag 1 is bent in annularly along the first fold 2. The first sealing lip 10 is thereby pressed against the inner wall surface of the respiration bag 1. Several clamps 9 can be provided additionally as mechanical holders and fix the respiration bag 1 in its bent-in position II having the reduced volume as shown in FIG. 2. Not shown in FIG. 2 is a position of the respiration bag 1 wherein the bag is bent in annularly along the second fold 11. This position is, in addition to position II, likewise possible and would additionally reduce the volume of the respiration bag 1.

It is understood that the foregoing description is that of the preferred embodiments of the invention and that various changes and modifications may be made thereto without departing from the spirit and scope of the invention as defined in the appended claims.

What is claimed is:

1. A respiration bag having at least one connecting stub, the respiration bag comprising:
    a bag-shaped hollow body defining a longitudinal axis having a direction;
    at least one fold region extending annularly over said body;
    said bag-shaped body being foldable in the direction of said longitudinal axis from a first stable position wherein said hollow body extends smoothly over said fold region to a second stable position wherein said bag-shaped body is bent inwardly in the direction of said axis at said fold region to define an annular fold in said fold region; and,
    holding means for responding to pressure within said bag-shaped hollow body to hold said hollow body in said second stable state during operational use of said respiration bag.

2. The respiration bag of claim 1, wherein said bag-shaped hollow body has a volume between 1600 and 1800 milliliters in said first stable position and a volume between 1000 and 1400 milliliters in said second stable position.

3. The respiration bag of claim 1, further comprising a plurality of mechanical holders which are applied externally on said annular fold to fix said bag-shaped hollow body in said second stable position.

4. The respiration bag of claim 1, wherein said bag-shaped body remains stable up to an inner pressure of 45 to 50 millibar.

5. The respiration bag of claim 1, wherein said at least one fold region is a first fold region and said annular fold is a first annular fold; and, wherein said respiration bag comprises a second fold region extending annularly over said body parallel to said first fold region; and, said bag-shaped body is foldable in the direction of said axis from said first stable position to a third stable position wherein said bag-shaped body is bent inwardly in the direction of said axis at said second fold region to define a second annular fold in said second fold region.

6. The respiration bag of claim 5, wherein said bag-shaped hollow body has an inner wall surface and a section which remains unchanged in all of said first, second and third stable positions; said holding means being a first holding means comprising a first sealing lip formed along said first annular fold so as to extend essentially parallel to the inner wall surface of said bag-shaped hollow body and said first sealing lip has a free edge which extends in the direction of said section when viewed from said first annular fold; and, said respiration bag further comprising a second holding means for responding to pressure within said bag-shaped hollow body to hold said hollow body in said third stable state during operational use of said respiration bag and said second holding means comprising a second sealing lip formed along said second annular fold so as to extend essentially parallel to the inner wall surface of said bag-shaped hollow body and said second sealing lip has a free edge which extends in the direction of said section when viewed from said second annular fold.

7. The respiration bag of claim 6, further comprising a plurality of mechanical holders which are applied externally on said second annular fold to fix said bag-shaped hollow body in said third stable position.

8. A respiration bag having at least one connecting stub, the respiration bag comprising:
    a bag-shaped hollow body defining a longitudinal axis having a direction;
    at least one fold region extending annularly over said body;
    said bag-shaped body being foldable in the direction of said longitudinal axis from a first stable position wherein said hollow body extends smoothly over said fold region to a second stable position wherein said bag-shaped body is bent inwardly in the direction of said axis at said fold region to define an annular fold in said fold region;

said bag-shaped hollow body has an inner wall surface and a section which remains unchanged in both of said first and second stable positions; and, said respiration bag further comprises a sealing lip formed along said fold so as to extend essentially parallel to the inner wall surface of said bag-shaped hollow body and said sealing lip has a free edge which extends in the direction of said section when viewed from said fold and moves toward and against said inner wall surface when said bag-shaped body is folded into said second stable position so as to permit inner pressure to act on said sealing lip thereby countering an unintended flip over of the respiration bag back into said first stable position.

* * * * *